United States Patent [19]

Saito et al.

[11] Patent Number: 4,876,026

[45] Date of Patent: Oct. 24, 1989

[54] OPTICALLY ACTIVE-2-METHYLBUTYRATE AND MATERIALS USING THE SAME

[75] Inventors: Shinichi Saito; Hiromichi Inoue; Kazutoshi Miyazawa; Kouji Ohno; Makoto Ushioda, all of Kanagawa, Japan

[73] Assignee: Chisso Corporation, Ohsaka, Japan

[21] Appl. No.: 134,295

[22] Filed: Dec. 15, 1987

[30] Foreign Application Priority Data

Dec. 26, 1986 [JP] Japan .................. 61-313308

[51] Int. Cl.$^4$ ............... G02F 1/13; C09K 19/34; C07D 239/02; C07D 211.72; C07D 211.84

[52] U.S. Cl. ............... 252/299.61; 252/299.01; 252/299.66; 350/350 R; 350/350 S; 544/315; 544/316; 544/318; 544/334; 544/335; 546/290; 546/300; 546/301; 546/302; 546/303; 546/330; 546/339; 546/341; 558/414; 560/141

[58] Field of Search ............ 252/299.61, 299.66, 252/299.01; 350/250 R, 250 S; 558/414; 560/141; 544/315, 316, 318, 335, 334; 546/290, 300-303, 330, 339, 341

[56] References Cited

U.S. PATENT DOCUMENTS

| | | | |
|---|---|---|---|
| 4,572,413 | 6/1988 | Inoue et al. | 252/299.61 |
| 4,592,858 | 6/1986 | Higuchi et al. | 252/299.66 |
| 4,684,477 | 8/1987 | Sugimori et al. | 252/299.61 |
| 4,695,651 | 9/1987 | Higuchi et al. | 252/299.66 |
| 4,697,015 | 9/1987 | Kano et al. | 252/299.61 |
| 4,723,018 | 2/1988 | Shionozaki et al. | 252/299.61 |
| 4,725,688 | 2/1988 | Taguchi et al. | 252/299.61 |
| 4,728,458 | 3/1988 | Higuchi et al. | 252/299.01 |
| 4,765,924 | 8/1988 | Inoue et al. | 252/299.61 |
| 4,781,857 | 11/1988 | Inoue et al. | 252/299.61 |
| 4,784,792 | 11/1988 | Inoue et al. | 252/299.61 |

FOREIGN PATENT DOCUMENTS

| | | | |
|---|---|---|---|
| 225195 | 6/1987 | European Pat. Off. | 252/299.61 |
| 248335 | 12/1987 | European Pat. Off. | 252/299.61 |
| 260077 | 3/1988 | European Pat. Off. | 252/299.61 |
| 367758 | 5/1988 | European Pat. Off. | 252/299.61 |
| 284008 | 9/1988 | European Pat. Off. | 252/299.61 |
| 2257588 | 6/1973 | Fed. Rep. of Germany | 252/299.61 |
| 3515373 | 11/1986 | Fed. Rep. of Germany | 252/299.61 |
| 2600052 | 7/1987 | Fed. Rep. of Germany | 252/299.61 |
| 240385 | 10/1986 | German Democratic Rep. | 252/299.61 |
| 240386 | 10/1986 | German Democratic Rep. | 252/299.61 |
| 60-54371 | 3/1985 | Japan | 252/299.61 |
| 63-182395 | 7/1988 | Japan | 252/299.61 |
| 8600067 | 1/1986 | World Int. Prop. O. | 252/299.61 |
| 8606401 | 11/1986 | World Int. Prop. O. | 252/299.61 |

Primary Examiner—Teddy S. Gron
Attorney, Agent, or Firm—Wenderoth, Lind & Ponack

[57] ABSTRACT

An optically active-2-methylbutyrate capable of imparting a spontaneous polarization value to achiral smectic compositions and also constituting ferroelectric liquid crystal compositions exhibiting a fast response at room temperature, and a liquid crystal composition containing the same, and further a light-switching element therefrom, are provided, which optically active-2-methylbutyrate is expressed by the formula

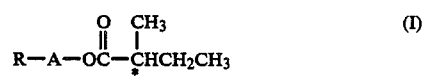

(I)

wherein R represents a linear or branched alkyl group or alkoxy group, each of 1 to 18 carbon atoms; A represents

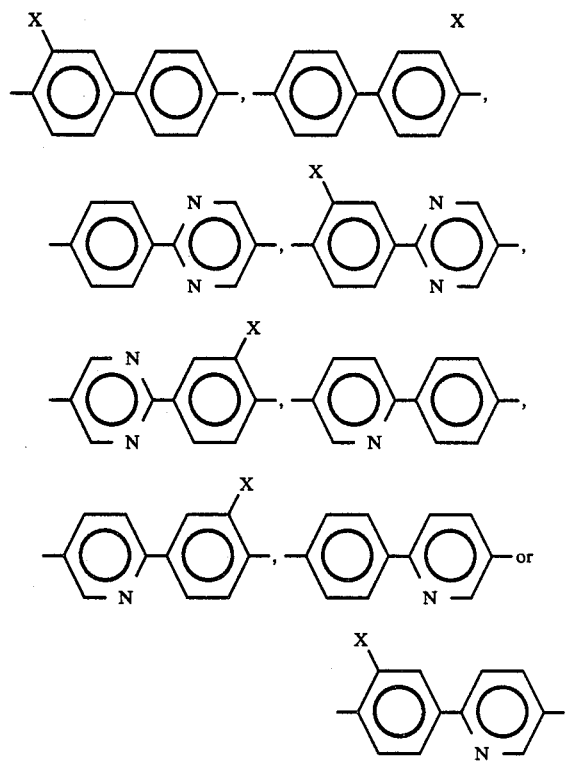

wherein X represents any one of F, Cl, Br or cyano group; and * indicates an optically active carbon atom.

5 Claims, No Drawings

OPTICALLY ACTIVE-2-METHYLBUTYRATE AND MATERIALS USING THE SAME

BACKGROUND OF THE INVENTION

1. Field of the Invention

This invention relates to an optically active-2-methylbutyrate, and more particularly it relates to a chiral substance having an optically active group and being suitable as a component of liquid crystal compositions and materials using the same such as ferroelectric liquid crystal compositions.

2. Description of the Related Art

At present, ferroelectric liquid crystals have been noted as materials for display elements. The display mode of the liquid crystals utilizes phases of chiral smectic C, F, G, H, I, etc. exhibiting ferroelectricity. Materials suitable to this display mode have been reported in various publications, but those shortening the response time of display elements have not been found.

SUMMARY OF THE INVENTION

The object of the present invention is to provide a compound shortening the response time of liquid crystal display elements and a liquid crystal composition and an element using the compound.

The present invention resides in, an optically active-2-methylbutyrate expressed by the formula $$R-A-O\overset{O}{\overset{\|}{C}}-\overset{*}{C}H(CH_3)CH_2CH_3 \qquad (I)$$

wherein R represents a linear or branched chain alkyl group of alkoxy group, each of 1 to 18 carbon atoms; A represents

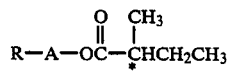

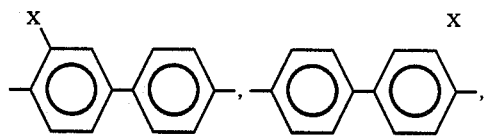

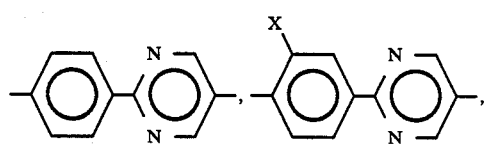

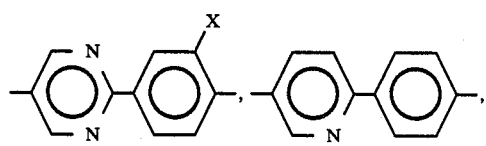

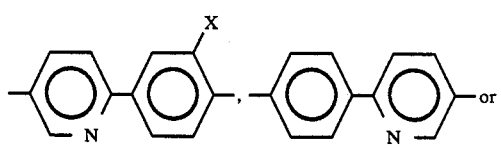

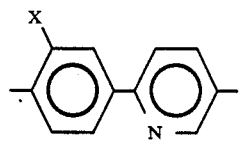

wherein X represents any one of F, Cl, Br or cyano group; and * indicates an optically active carbon atom, and a liquid crystal composition containing the compound, particularly a ferroelectric liquid crystal composition exhibiting chiral smectic phases, a liquid crystal composition exhibiting chiral nematic phases, and further a light-switching element using the above-mentioned ferroelectric liquid crystal composition.

DETAILED DESCRIPTION OF PREFERRED EMBODIMENTS

Among the groups of A enumerated above,

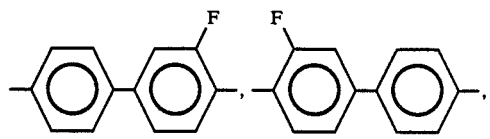

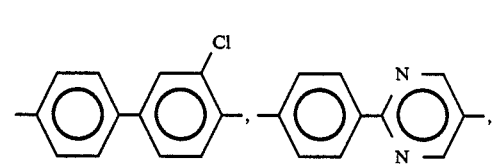

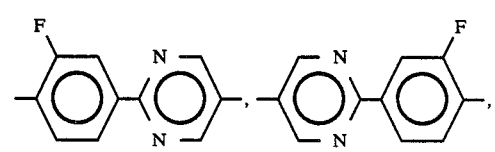

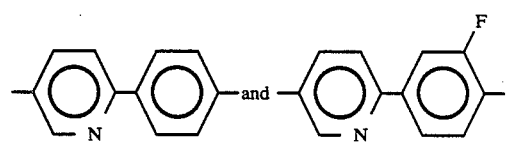

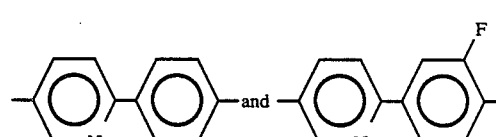

are preferred. R is preferably a linear or branched chain alkyl group or alkoxy group each of 4 to 16 carbon atoms, more preferably a linear or branched chain alkyl group of alkoxy group each of 6 to 12 carbon atoms. The absolute configuration of the compound may be either one of S-form or R-form, but since the compound of S-form is easily commercially available, it is practically preferable.

The phase transition points of representative examples of the compound of the present invention are shown in the following Table 1.

TABLE 1

| Sample No. | In the formula (I) R | A | Absolute configuration | Phase transition point Cr | Sc* | S$_A$ | I | Remarks |
|---|---|---|---|---|---|---|---|---|
| 1 | n-C$_{10}$H$_{21}$— | 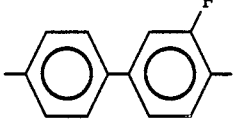 | S | . 26.1 | — | — | . | |
| 2 | n-C$_{12}$H$_{25}$— | 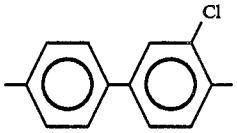 | S | . 14.1 | — | — | . | |
| 3 | n-C$_6$H$_{13}$— | 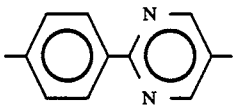 | S | . 56.3 | — | — | . | |
| 4 | n-C$_{10}$H$_{21}$— | " | S | . 53.4 | — | — | . | |
| 5 | n-C$_4$H$_9$O— | " | S | . 67.9 | — | — | . | |
| 6 | n-C$_8$H$_{17}$O— | " | S | . 61.3 | — | — | . | |
| 7 | n-C$_8$H$_{17}$— | 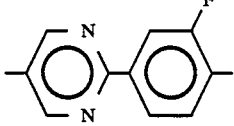 | S | . 44.8 | — | — | . | |
| 8 | n-C$_8$H$_{17}$— | 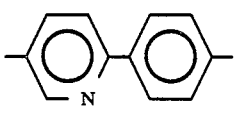 | S | . 36.5 | — | . 39.1 | . | Example 1 |
| 9 | n-C$_{10}$H$_{21}$— | " | S | . 27.0 | . 47.1 | — | . | |
| 10 | n-C$_8$H$_{17}$— | 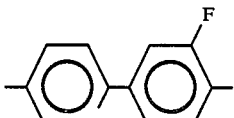 | S | . 7.4 | . 28.3 | — | . | |
| 11 | n-C$_9$H$_{19}$— | " | S | . 15.0 | . 25.6 | . 32.5 | . | Example 2 |

A specific feature of the compound of the present invention consists in that when the compound is added in a suitable quantity to achiral or chiral smectic liquid crystal compounds and/or compositions, the spontaneous polarization value (hereinafter abbreviated to Ps) of the resulting ferroelectric liquid crystal compositions notably increases as compared with that prior to the addition. When ferroelectric liquid crystals are made up into display elements, it is said that the Ps thereof is in inverse proportion to the response time. Thus, the larger the Ps, the shorter the response time. In addition, since liquid crystal compounds or compositions exhibiting phases of achiral smectic C, etc. are not ferroelectric liquid crystal compounds, Ps is absent. However, compositions obtained by adding the compound of the present invention to the above substances very often exhibit ferroelectric liquid crystalline phases, and the resulting ferroelectric liquid crystals have a notably large Ps. Further, when the compound of the present invention is added in a suitable quantity to ferroelectric liquid crystal compound or compositions having a very small Ps, the resulting substances have a notably large Ps. Thus, the response time is shortened as compared with that prior to the addition. In view of the above facts, the compound of the present invention is suitable as a component for increasing the Ps of ferroelectric liquid crystal compositions and shortening the response time.

Further, liquid crystal compositions containing the compound of the present invention as a chiral component exhibit an intrinsic chiral nematic pitch, cholesteric pitch or chiral smectic pitch in chiral nematic phases or chiral smectic phases.

In ferroelectric liquid crystal display, it is said that the length of chiral pitch has a great influence upon molecular alignment. The compound of the formula (I) may be suitably used for adjusting such chiral nematic pitch, cholesteric pitch and chiral smectic pitch.

Further, since the compound of the formula (I) of the present invention is a directly bonded bicyclic compound, its viscosity is low so that it also contributes to high rate response properties of liquid crystal compositions.

Further, since the compound of the formula (I) of the present invention has an optically active carbon atom, it has a capability of inducing a twisted structure when it is added to nematic liquid crystals. Nematic liquid crystals having a twisted structure, i.e. chiral nematic liquid crystals, do not form the so-called reverse domain (striped pattern) of TN mode elements; hence the compound of the formula (I) is usable as an agent for preventing the reverse domain from forming.

The compound of the formula (I) may be prepared as follows:

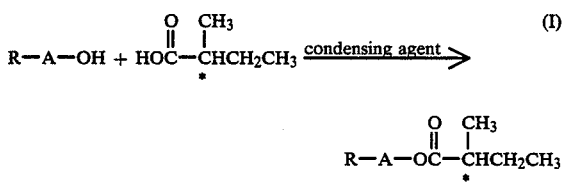

wherein R, A and * are defined above.

Namely, by reacting an optically active-2-methyl-butanoic acid with a phenol is the presence of a condensing agent, the objective optically active-2-methyl-butyrate is obtained. The above optically active-2-methyl-butanoic acid is suitably obtained by oxidizing optically active-2-methyl-butanol with potassium permanganate or the like. Further, as the condensing agent, N,N-dicyclohexylcarbodiimide, etc. are preferred.

Next, names of main compounds thus obtained other than the compounds of the present invention shown in Table 1 are as follows:

4'-butyl-3-fluoro-4-(2-methylbutanoyloxy)-biphenyl,
4'-pentyl-3-fluoro-4-(2-methylbutanoyloxy)-biphenyl,
4'-hexyl-3-fluoro-4-(2-methylbutanoyloxy)-biphenyl,
4'-heptyl-3-fluoro-4-(2-methylbutanoyloxy)-biphenyl,
4'-octyl-3-fluoro-4-(2-methylbutanoyloxy)-biphenyl,
4'-nonyl-3-fluoro-4-(2-methylbutanoyloxy)-biphenyl,
4'-undecyl-3-fluoro-4-(2-methylbutanoyloxy)-biphenyl,
4'-dodecyl-3-fluoro-4-(2-methylbutanoyloxy)-biphenyl,
4'-hexyl-3-chloro-4-(2-methylbutanoyloxy)-biphenyl,
4'-heptyl-3-chloro-4-(2-methylbutanoyloxy)-biphenyl,
4'-octyl-3-chloro-4-(2-methylbutanoyloxy)-biphenyl,
4'-nonyl-3-chloro-4-(2-methylbutanoyloxy)-biphenyl,
4'-decyl-3-chloro-4-(2-methylbutanoyloxy)-biphenyl,
4'-undecyl-3-chloro-4(2-methylbutanoyloxy)-biphenyl,
2-(4'pentylphenyl)-5-(2-methylbutanoyloxy)-pyrimidine,
2-(4'-heptylphenyl)-5-(2-methylbutanoyloxy)-pyrimidine,
2-(4'-octylphenyl)-5-(2-methylbutanoyloxy)-pyrimidine,
2-(4'-nonylphenyl)-5-(2-methylbutanoyloxy)-pyrimidine,
2-(4'-undecylphenyl)-5-(2-methylbutanoyloxy)-pyrimidine,
2-(4'-dodecylphenyl)-5-(2-methylbutanoyloxy)-pyrimidine,
2-(4'-pentyloxyphenyl)-5-(2-methylbutanoyloxy)-pyrimidine,
2-(4'-hexyloxyphenyl)-5-(2-methylbutanoyloxy)-pyrimidine,
2-(4'-heptyloxyphenyl)-5-(2-methylbutanoyloxy)-pyrimidine,
2-(4'-nonyloxyphenyl)-5-(2-methylbutanoyloxy)-pyrimidine,
2-(4'-decyloxyphenyl)-5-(2-methylbutanoyloxy)-pyrimidine,
2-(4'-undecyloxyphenyl)-5-(2-methylbutanoyloxy)-pyrimidine,
2-(4'-dodecyloxyphenyl)-5-(2-methylbutanoyloxy)-pyrimidine,
5-hexyl-2-(3'-fluoro-4'-(2-methylbutanoyloxy)-phenyl)-pyrimidine,
5-heptyl-2-(3'-fluoro-4'-(2-methylbutanoyloxy)-phenyl)-pyrimidine,
5-nonyl-2-(3'-fluoro-4'-(2-methylbutanoyloxy)-phenyl)-pyrimidine,
5-decyl-2-(3'-fluoro-4'-(2-methylbutanoyloxy)-phenyl)-pyrimidine,
5-undecyl-2-(3'-fluoro-4'-(2-methylbutanoyloxy)-phenyl)-pyrimidine,
5-dodecyl-2-(3'-fluoro-4'-(2-methylbutanoyloxy)-phenyl)-pyrimidine,
5-hexyl-2-(4'-(2-methylbutanoyloxy)-phenyl)-pyridine,
5-heptyl-2-(4'-(2-methylbutanoyloxy)-phenyl)-pyridine,
5-nonyl-2-(4'-(2-methylbutanoyloxy)-phenyl)-pyridine,
5-undecyl-2-(4'-(2-methylbutanoyloxy)-phenyl)-pyridine,
5-dodecyl-2-(4'-(2-methylbutanoyloxy)-phenyl)-pyridine,
5-hexyl-2-(3'-fluoro-4'-(2-methylbutanoyloxy)-phenyl)-pyridine,
5-heptyl-2-(3'-fluoro-4'-(2-methylbutanoyloxy)-phenyl)-pyridine,
5-decyl-2-(3'-fluoro-4'-(2-methylbutanoyloxy)-phenyl)-pyridine,
5-undecyl-2-(3'-fluoro-4'-(2-methylbutanoyloxy)-phenyl)-pyridine, and
5-dodecyl-2-(3'fluoro-4'-(2-methylbutanoyloxy)-phenyl)-pyridine.

The present invention will be described in more detail by way of Examples.

EXAMPLE 1

Preparation of (S)-4-(5'-octyl-2'-pyridinyl)-phenyl 2-methylbutyrate (A compound of the formula (I) wherein R represents octyl and A represents

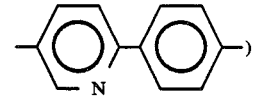

A mixture of (S)-(+)-2-methylbutanoic acid (0.5 g), N,N-dicylohexylcarbodiimide (1.3 g), 4-N,N-diemethylaminopyridine (0.1 g), 4-(5'-octyl-2'-pyridinyl)-phenol (1.25 g) and anhydrous dichloromethane 950 ml) was agitated at room temperature for 6 hours, followed by filtering off deposited solids, washing the solution with an acid, then with an alkali, and further with water, drying, purifying the resulting material according to column chromatography using a column filled with activated alumina, and twice carrying out recrystallization from ethanol to obtain the objective (S)-4-(5'-octyl-2'-pyridinyl)-phenyl 2-methylbutyrate (0.9 g). This product exhibited phase transitions of Cr (36.5° C.), SA (39.1° C.) and I wherein Cr, SA and I are abbreviations of liquid crystalline phase, smectic A phase and isotropic liquid phase, respectively; hereinafter these abbreviations are used as above.

EXAMPLE 2

Example 1 was repeated except that 4-(5''-octyl-2'-pyridinyl)-phenol in Example 1 was replaced by 2-fluoro-4-(5'-nonyl-2'-pyridinyl)-phenol, to obtain (S)-2-fluoro-4-(5'-nonyl-2'-pyridinyl)-phenyl 2-methylbutyrate (a compund of the formula (I) wherein R represents nonyl and A represents

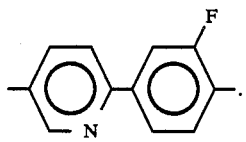

This product exhibited phase transitions of Cr (15.0°0 C.), SC* (25.6° C.), SA (32.5° C.) and I. SC* represents an abbreviation of chiral smectic C phase.

EXAMPLE 3

(Use example 1)

(S)-2-Fluoro-4-(5'-nonyl-2'-pyridinyl)-phenyl 2-methylbutyrate obtained in Example 2 was filled in a cell of 2 μm thickness provided with transparent electrodes each obtained by applying polyvinyl alcohol as an aligning agent onto the surface and rubbing the resulting surface to subject it to a parallel aligning treatment, to thereby obtain an element. This element was provided between two sheets of crossed polarizers, followed by impressing an electric field. As a result, change in the intensity of transmitted light was observed by impressing ±10 V. Response time was sought from the change in the intensity of transmitted light at that time, and Ps was sought according to Sowyer-Tower method.

The results are shown in the following Table 2:

TABLE 2

| Temperature (°C.) | Response time (μsec) | Ps (nC cm$^{-2}$) |
| --- | --- | --- |
| 25 | 20 | 10.3 |
| 20 | 45 | 23.9 |
| 15 | 65 | 30.4 |
| 10 | 90 | 34.2 |
| 5 | 110 | 39.3 |
| 0 | 150 | 45.4 |

As illustrated above, among the compounds of the formula (I) of the present invention, those which singly exhibit ferroelectric liquid crystalline phases are a superior material for ferroelectric liquid crystal display elements exhibiting a response time of 50 μ sec or less at room temperature.

EXAMPLE 4

(Use example 2)

A liquid crystal composition A consisting of
2-(4'-hexyloxyphenyl)-5-octyl-pyrimidine
 (30% by weight),
2-(4'-octyloxyphenyl)-5-octyl-pyrimidine
 (20% by weight),
2-(4'-nonyloxyphenyl)-5-octyl-pyrimidine
 (10% by weight),
2-(4'-decyloxyphenyl)-5-octyl-pyrimidine
 (10% by weight),
2-(4'-pentyl-4-biphenylyl)-5-octyl-pyrimidine
 (20% by weight), and
2-(4'-heptyl-4-biphenylyl)-5-octyl-pyrimidine
 (10% by weight),
exhibits phase transitions of Cr (4° C.), SC (65° C.), SA (79° C.), N (90° C.) and I wherein SC and N represent abbreviations of smectic C phase and nematic phase, respectively.

A mixture (composition B) of the above composition A (80% by weight) with (S)-4-(5'-octyl-2'-pyridinyl)-phenyl 2-methylbutyrate (a compound of No. 8 in Table 1) (20% by weight) exhibited phase transitions of SC* (53° C.), SA (67° C.), Ch (76.9° C.) and I wherein Ch represents an abbreviation of cholesteric phase, but its melting point was unclear. The response time and Ps of this composition B were sought under the same conditions as in Example 4.

The results were as follows:
110 μ sec and 1.3 nC cm$^{-2}$ at 50° C.;
145 μ sec and 2.0 nC cm$^{-2}$ at 40° C.;
200 μ sec and 2.2 nC cm$^{-2}$ at 30° C.: and
300 μ sec and 2.6 nC cm$^{-2}$ at 20° C.

EXAMPLE 5

(Use example 3)

A nematic liquid crystal composition consisting of

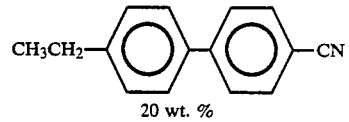

20 wt. %

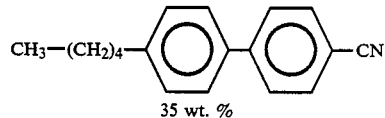

35 wt. %

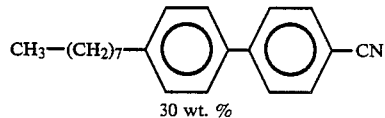

30 wt. % and

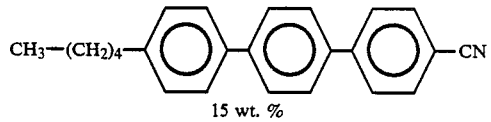

15 wt. % was filled in a cell provided with transparent electrodes each obtained by applying polyvinyl alcohol (PVA) as an aligning agent onto the surface and rubbing the resulting surface to subject it to a parallel aligning treatment and having a distance between the electrodes of 10 μm, to prepare TN mode display cell, which was then observed under a polarizing microscope. As a result, formation of a reverse twist domain was observed. To this nematic liquid crystal composition was added compound No. 8 in Table 1 in a quantity of 0.5% by weight and the resulting composition was similarly observed by means of the TN mode cell. As a result, no reverse domain was formed and a uniform nematic phase was observed.

EXAMPLE 6

(Use example 4)

To a nematic liquid crystal composition (ZLI-1132, manufactured by Merck Company) was added compound No. 5 in Table 1, i.e.,

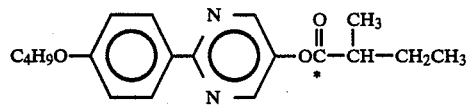

in a quantity of 5% by weight to prepare a chiral nematic liquid crystal composition. The chiral pitch of this composition was measured according to Cano-Wedge method. The results were as follows:

| Temperature (° C.) | Pitch (μm) |
| --- | --- |
| 20 | 34.2 |
| 30 | 34.0 |
| 40 | 34.4 |
| 50 | 36.4 |
| 60 | 39.8 |

The chiral nematic liquid crystal composition obtained by adding a compound of the present invention has a flat temperature-dependency of chiral pitch as seen above.

As apparent from the foregoing, by using the compound (I) of the present invention, it is possible to impart Ps to achiral smectic compositions and also to constitute ferroelectric liquid crystal compositions exhibiting a fast response at room temperature. Further, by adding the compound of the present invention in a suitable quantity to nematic liquid crystal compositions, it is possible to prevent reverse domain from forming.

What we claim is:

1. An optically active-2-methylbutyrate expressed by the formula

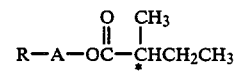

wherein R represents a linear or branched chain alkyl group or alkoxy group, each of 4 to 12 carbon atoms; A represents

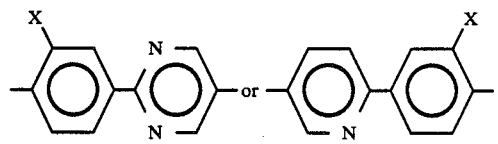

wherein X represents F or H; and * indicates an optically active carbon atom.

2. An optically active-2-methylbutyrate according to claim 1, where A is

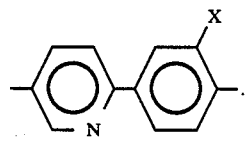

3. An optically active-2-methylbutyrate according to claim 1, where A is

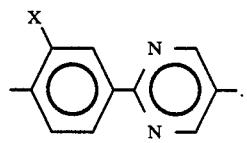

4. A ferroelectric liquid crystal composition comprising at least two components at least one of which is an optically active-2-methylbutyrate as set forth in claim 1.

5. A light switching element comprising a ferroelectric liquid crystal composition as set forth in claim 4.

* * * * *